US008765178B2

(12) United States Patent
Parikh et al.

(10) Patent No.: US 8,765,178 B2
(45) Date of Patent: Jul. 1, 2014

(54) CONTROLLED RELEASE FORMULATIONS AND ASSOCIATED METHODS

(75) Inventors: Nilesh H. Parikh, Irvine, CA (US); Teshome Melaku, Corona, CA (US)

(73) Assignee: Watson Laboratories, Inc., Salt Lake City, UT (US)

( * ) Notice: Subject to any disclaimer, the term of this patent is extended or adjusted under 35 U.S.C. 154(b) by 927 days.

(21) Appl. No.: 11/458,651

(22) Filed: Jul. 19, 2006

(65) Prior Publication Data

US 2008/0020039 A1    Jan. 24, 2008

(51) Int. Cl.
*A61K 9/22* (2006.01)
*A61K 9/24* (2006.01)
*A61K 31/44* (2006.01)

(52) U.S. Cl.
USPC .......................... 424/468; 424/472; 514/282

(58) Field of Classification Search
USPC ................... 424/468, 472; 514/282
See application file for complete search history.

(56) References Cited

U.S. PATENT DOCUMENTS

| | | | |
|---|---|---|---|
| 3,146,169 A | | 8/1964 | Stephenson et al. |
| 4,569,937 A | | 2/1986 | Baker et al. |
| 4,844,907 A | | 7/1989 | Elger et al. |
| 5,164,398 A | | 11/1992 | Sims et al. |
| 5,422,123 A | | 6/1995 | Conte et al. |
| 5,626,874 A | * | 5/1997 | Conte et al. .................. 424/464 |
| 5,783,212 A | * | 7/1998 | Fassihi et al. ................ 424/472 |
| 5,827,537 A | | 10/1998 | Palepu et al. |
| 5,968,551 A | | 10/1999 | Oshlack et al. |
| 6,087,386 A | | 7/2000 | Chen et al. |
| 6,348,216 B1 | | 2/2002 | Kushla et al. |
| 6,361,794 B1 | | 3/2002 | Kushla et al. |
| 6,663,892 B1 | | 12/2003 | Thassu |
| 6,696,066 B2 | | 2/2004 | Kaiko et al. |
| 6,699,502 B1 | | 3/2004 | Fanara et al. |
| 6,706,283 B1 | | 3/2004 | Appel et al. |
| 6,733,783 B2 | | 5/2004 | Oshlack et al. |
| 6,787,155 B2 | | 9/2004 | Woolfe et al. |
| 6,787,157 B1 | | 9/2004 | Rosenberg et al. |
| 6,838,094 B2 | | 1/2005 | Grimmett et al. |

(Continued)

FOREIGN PATENT DOCUMENTS

| | | |
|---|---|---|
| EP | 0068838 | 1/1983 |
| EP | 0384514 | 8/1990 |

(Continued)

OTHER PUBLICATIONS

Michael Woodward; International Search Report in PCT/US07/16498; Aug. 8, 2008; 3 pages; ISA/US; Alexandria, VA; USA.

(Continued)

*Primary Examiner* — Aradhana Sasan
(74) *Attorney, Agent, or Firm* — Florek & Endres PLLC

(57) ABSTRACT

A pharmaceutical formulation having a geometric configuration that affects the release characteristics of active agents contained therein and associated methods are provided. In one aspect, a sustained release oral dosage pharmaceutical tablet may include a first layer having a first active agent, where the first layer is disposed between two adjacent controlled release layers, at least one of the adjacent layers including at least one second active agent. The two adjacent layers are arranged such that they cover a portion of the first layer. The two adjacent layers may be separate layers or they may be joined into a single continuous layer, depending on the overall configuration and geometric design of the oral dosage form.

27 Claims, 5 Drawing Sheets

(56) References Cited

U.S. PATENT DOCUMENTS

| | | |
|---|---|---|
| 7,682,633 B2 | 3/2010 | Matthews et al. |
| 7,682,634 B2 | 3/2010 | Matthews et al. |
| 7,815,934 B2 | 10/2010 | Boehm |
| 7,927,623 B2 | 4/2011 | Sugimoto et al. |
| 2002/0081333 A1 | 6/2002 | Oshlack et al. |
| 2002/0192277 A1 | 12/2002 | Oshlack et al. |
| 2003/0068375 A1 | 4/2003 | Wright et al. |
| 2003/0092724 A1 | 5/2003 | Kao et al. |
| 2003/0180361 A1 | 9/2003 | Oshlack et al. |
| 2003/0198677 A1 | 10/2003 | Pryce Lewis et al. |
| 2003/0206954 A1 | 11/2003 | Lerner et al. |
| 2004/0052843 A1 | 3/2004 | Lerner et al. |
| 2004/0115265 A1 | 6/2004 | Benkerrour et al. |
| 2004/0121001 A1 | 6/2004 | Oshlack et al. |
| 2004/0224020 A1 | 11/2004 | Schoenhard |
| 2005/0112195 A1 | 5/2005 | Cruz et al. |
| 2005/0158382 A1 | 7/2005 | Cruz et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |

FOREIGN PATENT DOCUMENTS

| | | |
|---|---|---|
| EP | 0619733 | 8/2001 |
| EP | 1007005 | 9/2004 |
| EP | 1600154 | 11/2005 |
| WO | WO99/13799 | 3/1999 |
| WO | WO00/18378 | 4/2000 |
| WO | WO00/51685 | 9/2000 |
| WO | WO01/58451 | 8/2001 |
| WO | 02/064119 | 8/2002 |
| WO | WO03/022252 | 3/2003 |
| WO | WO03/037244 | 5/2003 |
| WO | WO2004/026256 | 4/2004 |
| WO | WO2004/052289 | 6/2004 |
| WO | WO2004/056337 | 7/2004 |
| WO | WO2005/030181 | 4/2005 |
| WO | WO2005/042101 | 5/2005 |
| WO | WO2005/072079 | 8/2005 |
| WO | 2005/101983 | 11/2005 |
| WO | WO2006/022996 | 3/2006 |

OTHER PUBLICATIONS

Luo Xiaojian, "Studies on the Traditional Chinese Medicine Compound Recipe Danshen Multi-layer Sustained Release Tablets and its Evaluation in Vivo and in Vitro", Ph.D. thesis, Mar. 15, 2004, Shenyang Pharmaceutical University.

Dorothee Mulhausen, International Preliminary Report on Patentability in PCT/US2007/016498, Jan. 20, 2009, 4 pages, The International Bureau of WIPO, Geneva, Switzerland.

F. Robert for Michael Woodward, Written Opinion of the International Searching Authority in PCT/US2007/106498, Aug. 8, 2008, 3 pages, United States Patent and Trademark Office, Alexandria, Virginia.

* cited by examiner

CONTROLLED RELEASE FORMULATIONS AND ASSOCIATED METHODS

FIELD OF THE INVENTION

The present invention relates to controlled release oral dosage formulations and methods for the treatment of various medical conditions in a subject using such. Accordingly, this invention involves the fields of chemistry, pharmaceutical sciences, medicine and other health sciences.

BACKGROUND OF THE INVENTION

Combinational drug therapy has been used for years as a mechanism for either pharmacologically addressing conditions presenting multiple symptoms, or for providing greater relief of a single symptom without overdose. One classic example of combinational therapy for addressing multiple symptoms can be found in many over-the-counter cold and flu medicines. Such medicines often combine a nasal decongestant, such as pseudoephedrine with a cough suppressant, such as dextromethorphan HBr, and an analgesic/antipyretic agent, such as acetaminophen.

Pain is one example of a single symptom that can be treated with combinational therapy in order to avoid overdose or to at least minimize the total dose of a single analgesic agent and thereby potentially avoid or reduce adverse effects. Acute pain, often the result of a traumatic event, can be effectively treated with doses of short acting analgesics, such as opioids. Chronic pain, however, because of its occurrence frequency and/or sustained presence, requires either multiple daily doses of short acting analgesics, or longer acting analgesic formulations in order to obtain effective management.

Long acting or "sustained release" formulations have in fact, been found to be desirable in treating many chronic conditions, such as chronic pain, that would otherwise require inconvenient multiple daily doses. However, oral dosage sustained release formulations are often complicated in their design, and while effective for many single drug therapies, may present a number of challenges when attempting to formulate combinational drug therapy.

As a result, sustained release formulations that are simple in design and construction that can effectively accommodate multiple active agents in a stable manner, and which can provide effective combination drug therapy over sustained periods continue to be sought.

SUMMARY OF THE INVENTION

Accordingly, the present invention provides a pharmaceutical tablet having a geometric configuration that, when combined with specific compositions, dictates the release characteristics of active agents contained therein. In one aspect, the sustained release oral dosage pharmaceutical tablet may include a first layer having a first active agent, where the first layer is disposed between two adjacent controlled release layers, at least one of the adjacent layers including at least one second active agent. The two adjacent layers are arranged such that they cover a portion of the first layer. The two adjacent layers may be separate layers or they may be joined into a single continuous layer, depending on the overall configuration and geometric design of the oral dosage form. In some aspects, these geometrically configured pharmaceutical tablets can be further coated using functional and/or non-functional polymers with or without a portion of the first and/or second active agents.

Numerous first active agents are contemplated that can be delivered via the oral formulations of the present invention. However, in one aspect, the first active agent may be an opioid agonist. Though any opioid agonist may be delivered by the oral formulations according to aspects of the present invention, non-limiting examples may include alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, and salts, isomers and combinations thereof.

Similarly, numerous second active agents are contemplated that may be administered in combination with various first active agents. However, in one aspect, for example, the second active agent may be a non-opioid analgesic. Such analgesics are widely known, and may include, without limitation, acetaminophen, aspirin, a non-steroidal anti-inflammatory drug, a cyclooxegenase inhibitor, an NMDA receptor antagonists, GABA receptor agonists, muscle relaxants, and combinations thereof. In one specific aspect, the first active agent may be hydrocodone and the second active agent may be acetaminophen.

Various coatings may also be utilized to provide additional release properties to the oral formulation. For example, in one aspect the sustained release formulation may include an immediate release layer containing a third active agent, where the third active agent may be the same or different from the first active agent and/or the second active agent. In one specific aspect, the first active agent may be hydrocodone, the second active agent may be acetaminophen, and the third active agent may be hydrocodone. In another aspect, the immediate release layer may be an immediate release coating surrounding the pharmaceutical tablet.

In another aspect of the present invention, a sustained release pharmaceutical tablet may be provided that includes a first layer having a first active agent to be released over a sustained period of time and at least two adjacent layers being configured to regulate fluid access to a portion of the first layer, thereby controlling release of the first active agent from the first layer over the sustained period of time. The adjacent layers may include at least one second active agent to be released over a sustained period of time that is different from the first active agent.

In one specific aspect, the first active agent may be hydrocodone and the second active agent may be acetaminophen. In certain aspects, for example, a pharmaceutical formulation may be configured such that the first layer and the at least two adjacent layers provides a $T_{max}$ hydrocodone serum concentration occurring at about 3 hours or more after administration of the tablet to the subject. In another aspect, a pharmaceutical formulation may also be configured so that the first layer and the at least two adjacent layers provides a $T_{max}$ hydrocodone serum concentration at from about 3 hours to about 8 hours after administration of the tablet to the subject. In yet another aspect, a pharmaceutical formulation may further be configured so that the first layer and the at least two adjacent layers provides a $T_{max}$ hydrocodone serum concentration at from about 4 hours to about 8 hours after administration of the tablet to the subject. In a further aspect, a pharmaceutical formulation may further be configured so that the first layer and the at least two adjacent layers provides a $T_{max}$ hydrocodone serum concentration at from about 4 hours to about 6 hours after administration of the tablet to the subject.

Various methods of controlling administration of pharmaceutical agents are also contemplated as part of the present invention. For example, in one aspect a method for controlling drug release from an oral dosage formulation administered to a subject is provided. Such a method may include regulating exposure of a first active agent containing layer in the tablet to the subject's gastrointestinal fluid by placing said first layer between two adjacent controlled release layers having at least one second active agent In another aspect of the present invention, a method of limiting release acceleration of an active agent from a pharmaceutical formulation, when said formulation is exposed to alcohol, is provided. Such a method may include regulating fluid access to a portion of a first layer containing said active agent by placing said first layer in contact with at least one adjacent layer that regulates the first layer's exposure to alcohol. For example, the first layer may be placed between two adjacent layers where the adjacent layers control fluid access to a majority of the first layer's surface area. Additionally, in some aspects the adjacent layers may contain at least one second active agent.

In yet another aspect of the present invention, a pharmaceutical tablet that limits alcohol-induced accelerated release of an active agent is provided. Such a method may include a first layer having a first active agent, the first layer disposed between two adjacent layers, where at least one of the adjacent layers includes at least one second active agent. Additionally, the two adjacent layers cover a portion of the first layer such that, in an alcohol containing environment, alcohol access to a majority of the first layer's surface area is limited by the two adjacent layers upon ingestion.

In a further aspect of the present invention, a pharmaceutical tablet is provided that limits alcohol-induced accelerated release of an active agent. Such a tablet may include a first layer having a first active agent, the first layer disposed between two adjacent layers, where at least one of the adjacent layers includes at least one second active agent and covers a portion of the first layer. Additionally, such a tablet may provide a release rate of the first active agent into an in vitro solution of from about 30% to about 50% after about 1 hour, from about 45% to about 75% after about 2 hours, and from about 80% to about 100% after about 4 hours, where the in vitro solution includes up to about 40% ethanol.

In yet a further aspect, a sustained release oral dosage pharmaceutical tablet is provided, including a first layer including a first active agent, a first layer including a first active agent, the first layer disposed between two adjacent layers, at least one of which includes at least one second active agent. The two adjacent layers may cover a portion of the first layer in order to control release of the first active agent at a rate of from about 30% to about 45% after about 1 hour, from about 43% to about 75% after about 2 hours, and from about 80% to about 100% after about 4 hours.

DEFINITIONS OF KEY TERMS

Figure 1:
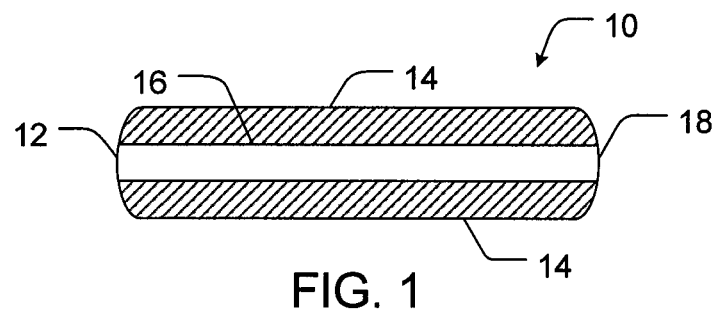
FIG. 1 is a cross-section view of a pharmaceutical tablet in accordance with one embodiment of the present invention.

In describing and claiming the present invention, the following terminology will be used in accordance with the definitions set forth below.

The singular forms "a," "an," and, "the" include plural referents unless the context clearly dictates otherwise. Thus, for example, reference to "a drug" includes reference to one or more of such drugs, and reference to "an excipient" includes reference to one or more of such excipients.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients.

As used herein, "active agent," "bioactive agent," "pharmaceutically active agent," and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts.

As used herein, "first active agent," "second active agent," and "third active agent" refer to active agents included in the formulations according to aspects of the present invention. It should be understood that the second active agent must be different from the first active agent. Additionally, the third active agent may be different from both the first and second active agent or the third active agent may be the same as either of the first or the second active agent.

As used herein, "between" refers to a first layer being located within an area bounded on at least two sides by adjacent layers. It should be understood that the first layer being located "between" two adjacent layers includes those situations where the first layer is in direct contact with the adjacent layers and those situations where the first layer is not in direct contact the one or more of the adjacent layers.

As used herein, "controlled release" refers to any form of drug release that is modified from immediate drug release.

Non-limiting examples of controlled release include sustained release, delayed release, pulsatile release, etc.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals.

As used herein, "blood level" may be used interchangeably with terms such as blood plasma concentration, plasma level, plasma concentration, serum level, serum concentration, serum blood level and serum blood concentration.

As used herein, "oral dosage form" and the like refers to a formulation that is ready for administration to a subject through the oral route of administration. Examples of known oral dosage forms, include without limitation, tablets, capsules, caplets, powders, pellets, granules, etc. Such formulations also include multilayered tablets wherein a given layer may represent a different drug. In some aspects, powders, pellets, and granules may be coated with a suitable polymer or a conventional coating material to achieve, for example, greater stability in the gastrointestinal tract, or to achieve the desired rate of release. Moreover, capsules containing a powder, pellets or granules may be further coated. Tablets and caplets may be scored to facilitate division of dosing. Alternatively, the dosage forms of the present invention may be unit dosage forms wherein the dosage form is intended to deliver one therapeutic dose per administration.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, "pharmaceutically acceptable carrier" and "carrier" may be used interchangeably, and refer to any inert and pharmaceutically acceptable material that has substantially no biological activity, and makes up a substantial part of the formulation.

The term "admixed" means that the drug and/or other ingredients can be dissolved, dispersed, or suspended in the carrier. In some cases, the drug may be uniformly admixed in the carrier.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

DETAILED DESCRIPTION

The present invention involves oral dosage forms for administering two or more active agents, at least one of which is administered over an extended or sustained period of time. In some aspects, such oral dosage forms may have multiple drug layers containing different active agents. The rate of release of an active agent from a drug layer of an oral dosage form is often dependent on the proportion of the surface area of the drug layer that is exposed to the aqueous environment of the gastrointestinal tract. This is particularly true of drug layers having a swellable/erodible matrix where an active agent is released as the matrix swells (i.e. hydrates) and erodes due to the aqueous environment. By physically controlling exposure of a portion of the surface area of a drug layer to the gastrointestinal environment, for example, by covering it with another drug containing layer, the rate of erosion and/or swelling of the covered layer may be controlled, and consequently, the release of drug contained therein may be controlled. In other words, the rate of release of the drug within the covered layer would be proportional to the amount of exposed surface area of that layer. Thus if the amount of exposed surface area remains constant, the rate of release of the drug from the covered layer remains relatively constant. Thus the rate of release of the drug may be controlled by controlling the exposed surface area of the layer containing the drug. As the controlling layer, or layers, swell (s), the diffusion of the drug within the hydrated layer increases, the surface area for release increases, and the diffusional distance for the drug decreases as the layers erodes. With further erosion, the surface area of the drug layer that is then directly exposed to the aqueous environment is effectively increased as well. These combined effects thus may increase the release of the active agent contained in the covered layer. Any second active agent contained within the adjacent layer can be released prior to and during the exposure of a major portion of the underlying drug layer and thus effective combinational therapy can be achieved.

The pharmaceutical compositions of the present invention are designed to provide combinational pharmacotherapy by including separate drug layers arranged to provide sustained release of at least one of the active agents contained in the composition. Referring now to FIG. 1, one aspect of the present invention is shown in which a pharmaceutical tablet 10 may include a first layer 12 that contains a first active agent. The first layer 12 is further disposed between two adjacent layers 14 containing at least one second active agent. By arranging the two adjacent layers 14 to cover a portion of the first layer 12, aqueous fluids are inhibited from directly contacting the covered portions 16 of the first layer 12 until they are exposed to the aqueous environment through erosion or swelling of the adjacent layers 14. It should be noted that such exposure may or may not occur simultaneously across all surface area of the first layer. Similarly, effective exposure and subsequent release of the first active agent from the covered areas of the first layer may occur prior to complete erosion of the adjacent layers as these layers swell with aqueous fluids. It should also be noted that each of the adjacent layers may not necessarily swell or erode at the same rate, and thus the first active agent may be released more quickly from one blocked or hindered surface as compared to another.

In one embodiment, it is intended that two adjacent layers 14 cover only a portion of the surface area of the first layer 12, and thus the formulation may contain a non-covered portion 18. In this way, the first active agent may begin to release from the non-covered portion 18 concurrent upon exposure to an aqueous environment. In certain aspects it is intended that the first active agent be primarily released via the non-covered portion 18 of the tablet prior to erosion of the adjacent layers 14. This configuration may allow the exposed surface area of the first layer 12 to remain constant, and thus to potentially approximate a constant and near zero-order release. In other aspects, release of the first active agent from the non-covered portions 18 may occur at a relatively consistent rate until the exposure of the covered portions 16, after which the rate of release of the first active agent will increase relative to the proportion of the exposed surface area of the first layer 12.

Additionally, the adjacent layers 14 may each contain the same second active agent, or they may each contain a different active agent. Non-limiting examples of active agents that may be included within the adjacent layers are described further herein. Further, the pharmaceutical composition may further include an outer coating, as is described herein. The outer coating may contain active agent that is the same as the first or second active agent, or that is different from the first and second active agent.

The pharmaceutical compositions of the present invention may include at least two active agents and at least one pharmaceutically acceptable carrier. The active agents and the pharmaceutically acceptable carrier are arranged into a first layer and at least two adjacent layers, as has been described. In some aspects, the compositions may also include at least one pharmaceutically acceptable excipient. The pharmaceutical compositions can also be provided in a wide variety of shapes, including circular, oval, oblong, triangular, polygonal, square, etc. The compositions may also be created in a variety of sizes. In one aspect, a tablet may have a size from about 0.1 inches to about 1.2 inches. In another aspect, a tablet may have a size range from about 0.2 inches to about 1.0 inches. In yet another aspect, a tablet may have a size range from about 0.4 to about 0.8 inches. Various caplet dimensions are also contemplated. In one aspect, for example, a caplet may be from about 0.1 inches to about 0.6 inches in width, and from about 0.2 inches to about 1.2 inches in length. In another aspect, a caplet may be from about 0.2 inches to about 0.4 inches in width, and from about 0.6 inches to about 0.9 inches in length.

Additionally, the various layers can be of any thicknesses that may be useful in a pharmaceutical formulation. For example, in one aspect either of the first layer or one of the adjacent layers may have a thickness of from about 0.05 inches to about 0.5 inches. In another aspect, either of the first layer or one of the adjacent layers can have a thickness of from about 0.05 inches to about 0.3 inches. In yet another aspect, either of the first layer or one of the adjacent layers can have a thickness of from about 0.075 inches to about 0.125 inches.

Numerous different first layer configurations are contemplated. Accordingly, the first layer can be configured to release the first active agent with various release profiles. Upon ingestion, release from the first layer will be limited to the exposed surface area, i.e. those regions not hindered by the adjacent layers. The initial rate of release of the first active agent from the first layer is therefore dependent on the proportion of exposed surface area of the first layer in a particular oral dosage form and the hydration characteristics of that layer due to fluid absorption. As the adjacent layers begin to degrade and/or swell, fluids begin to contact the blocked surface area of the first layer and the rate of release of the first active agent will accelerate in proportion to the exposed surface area. The release characteristics of the first active agent may be further altered, however, by utilizing extended release materials within the first layer. Thus the rate of release of the first active agent may be controlled primarily by the hindering action of the adjacent layers and secondarily by any sustained release properties of the matrix comprising the first layer, the erosion rate, and the solubility of the fist active agent. Although various release profiles may be achieved, in one aspect release of the first active agent from the formulation may occur at a relatively constant rate. Such constant release rates may be achieved by utilizing adjacent layers in the formulation that remain intact throughout most of the release duration of the first active agent. Such a formulation may maintain a relatively constant release rate, and in some aspects the first layer is exposed only around a peripheral edge throughout most of the release duration.

By arranging multiple pharmaceutical layers in particular geometries, various active agents can be released from an oral formulation in a sustained release manner that is dependent on the relative orientation of the layers. As previously noted, this may be accomplished by arranging particular layers to cover another layer, thus minimizing the aqueous exposure of the covered layer following ingestion. Thus multiple active agents having different release profiles can be provided in the same pharmaceutical formulation. This may be particularly effective for those drug combinations that are intended to work in tandem, whether synergistically enhancing or not.

In addition to the relative physical orientation of the first layer and the adjacent layers, the rate of erosion of each type of layer may contribute to the release profile of the pharmaceutical combination. For example, by formulating the adjacent layers to erode more slowly, the pharmaceutical combination will provide a longer $T_{max}$ and thus prolong the sustained release of the first active agent. Alternatively, by formulating the adjacent layers to erode more quickly, the pharmaceutical combination will provide a shorter $T_{max}$ and thus reduce the sustained release of the first active agent. Similarly, the rate of erosion of the adjacent layers can be utilized to reduce or prolong the release of both the second active agent and the first active agent.

The relative rates of erosion of the first layer and the adjacent layers may be selected to provide specific release profiles. For example, in one aspect the rates of erosion for the first layer and the adjacent layers may be the same. In another aspect, the adjacent layers may erode at a higher rate than the first layer. In yet another aspect, the adjacent layers may erode at a lower rate than the first layer. Additionally, it is contemplated that the adjacent layers may erode at different rates from one another. For example, in one aspect each of the adjacent layers may erode at different rates that are higher than the erosion rate of the first layer. In another aspect, each of the adjacent layers may erode at different rates that are lower than the erosion rate of the first layer. In yet another aspect, each of the adjacent layers may erode at different rates, one that is higher that the erosion rate of the first layer and one that is lower than the erosion rate of the first layer. In a further aspect, one adjacent layer may erode at the same rate as the first layer, and one adjacent layer may erode at a different rate than the first layer.

As the various layers hydrate, drug release occurs via erosion and diffusion through the respective hydrated layer. The degree of hydration and the solubility of the respective drug within the hydrated layer affect drug release. The rate of release of the first and second active agents may, therefore, also be affected by the solubilities of each of the active agents. How well an active agent is solubilized in the aqueous environment of the gastrointestinal tract is one factor that determines the time course of sustained release. Additionally, the solubility of the second active agent determines how rapidly the hindered portions of the first layer are exposed, and thus determines to some extent the time course of release of both active agents.

Accordingly, various factors such as the relative spatial relation of the first layer and the adjacent layers, hydration and erosion rates of the layers, the level of compression of the layers, and the solubilities of the active agents may determine the duration of the release of both the first and second active agents. Various durations for the sustained release of the first active agent are contemplated. For example, in one aspect the pharmaceutical composition may provide release of the first active agent for at least 4 hours. In another aspect, the pharmaceutical composition may provide release of the first active agent for at least 8 hours. In yet another aspect, the pharmaceutical composition may pros de release of the first active agent for at least 12 hours. In a further aspect, the pharmaceutical composition may provide release of the first active agent for at least 24 hours. In a yet further aspect, the pharmaceutical composition may provide release of the first active agent for at least 36 hours.

As has been described, in various aspects of the present invention, the second active agent may be provided as sustained release. As such, a broad range of release characteristics are contemplated. For example, in one aspect the pharmaceutical composition may provide release of the second active agent for at least 3 hours. In another aspect, the pharmaceutical composition may provide release of the second active agent for at least 6 hours. In yet another aspect, the pharmaceutical composition may provide release of the second active agent for at least 12 hours. In a further aspect, the pharmaceutical composition may provide release of the second active agent for at least 18 hours.

As has been described, the adjacent layers of the pharmaceutical compositions of the present invention may be utilized to physically block access of fluids to a portion of the first layer, thus controlling the surface area from which the first active agent can be released. The adjacent layers may be selected so as to erode over various durations. Accordingly, the adjacent layers may be designed to affect a sustained rate of release of the first active agent within a particular duration following ingestion of the oral dosage form, during which time the adjacent layers may release at least one second active agent as the layers erode. Numerous configurations of adjacent layers are contemplated to release at least one second active agent and to provide adequate hindrance to the first layer to affect sustained release of the first active agent therefrom. The rate of erosion of the adjacent layers may be further varied by including sustained release materials therein, or by including materials to allow a more rapid erosion of the adjacent layers.

The oral formulations and various layers as disclosed herein may be formed by any means known to one of ordinary skill in the art, such as by compression, molding, etc., provided that the formulations are constructed having layers with the relative geometries according to various aspects of the present invention. General methods for preparing oral solid dosage forms can be found in *Remington*, supra, Chapter 45, which is incorporated herein by reference.

Numerous active agents are contemplated that may be delivered from the sustained release oral formulations according to the aspects of the present invention. Thus the formulations are not limited to a particular class, but may include any combination of at least two active agents that can be delivered over an extended period of time. It is contemplated that the combinations of active agents may have related or unrelated actions. In some cases, the actions of the combination of active agents may be synergistically enhancing. Any drug combination known to one of ordinary skill in the art may be delivered together via the oral dosage formulations according to aspects of the present invention. Examples of major classes of drugs may include, without limitation, analgesics, cold and sinus medications, heart medications, blood pressure medication, lipid regulating medications, neurochemical modulators such as serotonin reuptake inhibitors, antibiotics, antivirals, and any other medication that can beneficially be administered as a sustained release formulation.

Additionally, various combinations of active agents may be formulated together to provide beneficial pharmaceutical compositions according to aspects of the present invention. Examples of such combinations may include, without limitation, combinations of analgesics, an analgesic and an anti-inflammatory agent, an antihistamine and a decongestant, an analgesic and an antihistamine or a decongestant, an analgesic and an antipyretic, an opioid analgesic and an antinausea agent, a muscle relaxant and a GABA receptor agonist, etc.

One class of active agents that can provide a benefit to a subject through sustained release delivery includes analgesic compounds. Typically, immediate release analgesics must be taken frequently, and tend to diminish in therapeutic effect during sleep. Sustained release analgesics may be highly beneficial to a subject because of reduced dosing frequency and extended sleep periods. As such, a combination of at least two analgesics can be administered according to aspects of the present invention to provide extended therapeutic relief from pain.

In one aspect of the present invention, at least one of the active agents in the oral formulation may include an opioid agonist. Examples of opioids agonists may include, without limitation, alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, and salts or combinations thereof. Various opioid agonists may contain one or more asymmetric centers and may thus give rise to enantiomer, diastereomer, and other stereoisomeric forms. The present invention is also meant to encompass all such possible forms as well as their racemic and resolved forms and mixtures thereof. When the compounds described herein contain olefinic double bond or other centers of geometric asymmetry, and unless specified otherwise, it is intended to include both E and Z geometric isomers. All tautomers are intended to be encompassed by the present invention as well.

In one aspect, the oral formulation may include at least one opioid agonist such as hydrocodone. Hydrocodone may also be included in the formulation as a salt. Suitable pharmaceutically acceptable salts of hydrocodone include hydrocodone bitartrate, hydrocodone bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone hemipentahydrate, hydrocodone pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis(heptafuorobutyrate), hydrocodone bis(methylcarbamate), hydrocodone bis(pentafluoropropionate), hydrocodone bis(pyridine carboxylate), hydrocodone bis(trifluoroacetate), hydrocodone chlorhydrate, and hydrocodone sulfate pentahydrate. In one specific aspect, the opioid agonist may be hydrocodone bitartrate.

One potential problem that may arise with any sustained release opioid agonist formulation is that of drug abuse. By crushing or chewing an oral formulation intended for sustained release, a higher concentration of the opioid agonist can be released immediately. To preclude such activity, a sequestered opioid antagonist may be included in the formulation. When such a tablet is crushed or chewed, the opioid antagonist is released along with the opioid agonist to compete with opioid receptors in the subject, thus reducing the effects of the agonist. Examples of opioid antagonists include, without limitation, naltrexone, naloxone, nalmefene, methylnaltrexone, naloxone methiodide, nalorphine, naloxonazine, nalide, nalmexone, nalbuphine, nalorphine dinicotinate, naltrindole, naltrindole isothiocyanate, naltriben, norbinaltorphimine, b-funaltrexamine, BNTX, cyprodime, etc.

Analgesic active agents may also include non-steroidal anti-inflammatory drug (NSAID) compounds. NSAIDs are drugs that may produce analgesic, antipyretic, and anti-inflammatory effects in a subject following administration. Many NSAIDs act as non-selective inhibitors of the enzyme cyclooxygenase, inhibiting both the cyclooxygenase-1 (COX-1) and cyclooxygenase-2 (COX-2) enzymes and thus exert effects through the arachidonic acid biochemical pathway. Examples of useful NSAIDs may include, without limitation, acetylsalicylic acid, methyl salicylate, diflunisal, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, ketorolac, tiaprofenic acid, fluprofen, bucloxic acid, indomethacin, sulindac, tolmetin, zomepirac, tiopinac, zidometacin, acemetacin, fentiazac, clidanac, oxpinac, mtfenamic acid, meclofenamic acid, flufenamic acid, niflumic acid, tolfenamic acid, diflurisal, flufenisal, piroxicam, sudoxicam or isoxicam, and the like. Such non-steroidal anti-inflammatory agents also include cyclo-oxygenase inhibitors such as celecoxib (SC-58635), DUP-697, flosulide (CGP-28238), meloxicam, 6-methoxy-2 naphthylacetic acid (6-MNA), VIOXX® (MK-966), nabumetone (prodrug for 6-MNA), nimesulide, NS-398, SC-5766, SC-58215, and T-614 as amantadine (1-aminoadamantine), and memantine (3,5 dimethylaminoadamantone), their mixtures and pharmaceutically acceptable salts thereof.

Useful analgesic agents may also include specific COX-2 inhibitors. It should be noted that there may be certain compounds that are classified as both NSAIDs and COX-2 inhibitors due to the inhibitory action of many NSAIDs on the cyclooxegenase-2 enzyme. As such, the categorization of a compound into a particular class should not be seen as limiting in any way. Non-limiting examples of COX-2 inhibitors may include valdecoxib (BEXTRA®), celecoxib (SC-58635; CELEBREX®), DUP-697, flosulide (CGP-28238), meloxicam, 6-methoxy-2 naphthylacetic acid (6-MNA), MK-966 (VIOXX®), nabumetone (prodrug for 6-MNA), nimesulide, NS-398, SC-5766, SC-58215, T-614; etc. Cyclooxygenase-3 (COX-3) inhibitors such as acetaminophen have also been reported in the art, and may be useful compounds to include in the sustained release dosage forms of the present invention.

N-methyl-D-aspartic acid (NMDA) receptor antagonists may also be included in the sustained release formulations of the present invention to provide therapeutic relief from pain. Non-limiting examples may include dextrorphan, dextromethorphan, ketamine, amantadine, memantine, eliprodil, ifenprodil, dizocilpine, remacemide, iamotrigine, riluzole, aptiganel, phencyclidine, flupirtine, celfotel, felbamate, spermine, spermidine, levemopamil, APV, and pharmaceutically acceptable salts, esters, metabolic precursors, or combinations thereof thereof.

Gamma-aminobutyric acid (GABA) agonists may also be included in the sustained release formulations of the present invention to provide various therapeutic effects, such as anti-anxiety effects, anti-convulsive effects, etc. Examples of GABA agonists may include, without limitation, avermectins such as doramectin, selamectin, and ivermectin, barbiturates, bicucullines, benzodiazepines, baclofen, cannibinoids, carbamazepines, cyclopyrrolone derivatives such as eszopiclone and zopiclone, ethanol, gabapentin, gabazine, gamma-hydroxybutyrate (GHB), imidazopyridines such as zaleplon and zolpidem, muscimol, phenyloin, picrotoxin, progabide, propofol, thujone, valproate, and pharmaceutically acceptable salts, esters, metabolic precursors, or combinations thereof.

The amount of an analgesic active agent to be orally administered may be measured according to several different parameters. In one aspect, the amount of an analgesic administered may be an amount sufficient to achieve a therapeutic effect. The amount required to obtain a therapeutic effect may vary depending on a number of factors, including the activity or potency of the specific analgesic active agent selected, as well as physiological variations among subjects as to drug tolerance and general metabolic issues. Particular combinations of analgesic active agents may also affect the amount of each be administered due to supportive or synergistic effects between the drugs. In one aspect, behavioral variation can provide some measure of therapeutic effectiveness. As such, it is well within the knowledge of those skilled in the art and in view of the present disclosure to determine dosages of analgesic active agents that are therapeutically effective for a given subject.

In one specific aspect of the present invention, a pharmaceutical formulation is provided having a sustained release first layer containing hydrocodone, two sustained release adjacent layers containing acetaminophen, and an immediate release outer layer containing hydrocodone. In one aspect, the immediate release outer layer may be an immediate release outer coating substantially surrounding the pharmaceutical tablet. Such a formulation may provide immediate release of hydrocodone upon ingestion for immediate relief of pain, and extended release of acetaminophen followed by extended release of hydrocodone for longer term pain relief. More specifically, upon ingestion the outer coating of the formulation begins immediate release of hydrocodone to provide quick pain relief to a subject. As the outer coating erodes away, the adjacent layers containing acetaminophen and a portion of the first layer containing hydrocodone are exposed. Following such exposure, acetopminophen is released from the adjacent layers and a portion of the hydrocodone is released from the exposed portions of the first layer. The amount of hydrocodone released from the first layer may be proportional to the amount of exposed surface area of that layer. As the adjacent layers expand and degrade, additional surface area of the first layer is exposed to the aqueous liquid thus increasing the amount of hydrocodone released therefrom.

Various dosages of hydrocodone may be used in the oral formulations according to aspects of the present invention. For example, in one aspect the hydrocodone may be present in an amount of from about 1 mg to about 40 mg. In another aspect, the hydrocodone may be present in an amount of from about 2 mg to about 25 mg. In yet another aspect, the hydrocodone may be present in an amount of from about 5 mg to about 20 mg. Similarly, various dosages of acetaminophen may be used in the oral formulations according to aspects of the present invention. For example, in one aspect the acetaminophen may be present in an amount of from about 50 mg to about 1500 mg. In another aspect the acetaminophen may be present in an amount of from about 100 mg to about 700 mg. In yet another aspect the acetaminophen may be present in an amount of from about 200 mg to about 500 mg.

Numerous pharmaceutically acceptable carriers can be utilized in the first layer and adjacent layers according to aspects of the present invention. A particular carrier may be selected due to erosion rate, compatibility with the active agent, or any other useful criteria. Examples of carriers may include, without limitation, lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose, and the like, as well as combinations thereof.

Various swellable and/or erodible polymers are contemplated for inclusion in the adjacent layers and the first layer. Specific polymers or combination of polymers may be selected in order to achieve particular swelling and/or erosion rates. Non-limiting examples of such polymers may include polylactides, polyglycolides, polylactide-co-glycolides, polylactic acids, polyglycolic acids, polylactic acid-co-glycolic acids, polycaprolactone, polycarbonates, polyesteramides, polyanhydrides, polyamino acids, polyorthoesters, polyacetyls, polycyanoacrylates, polyetheresters, polydioxanones, polyalkylene alkylates, copolymers of polyethylene glycol and polyorthoester, biodegradable polyurethanes, hydrogels, blends and copolymers thereof. Additional non-limiting examples may also include high molecular weight, water-soluble polymers such as polyethylene oxide and cellulosic polymer derivatives including hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyls, polyvinyl alcohol, polyacrylic acids, alginates, gelatin, natural gums, including guar, lightly crosslinked versions of these polymers, starches, starch graft copolymers and the like.

The sustained release formulations of the present invention may additionally include various pharmaceutically acceptable excipients. The selection of particular excipients for a given formulation may depend upon the active agents employed, the physical form of the various layers of the formulation, the time-course of the sustained release effects, and other factors. Non-limiting examples of excipients may include glucose, lactose, natural sugars such as sucrose, glucose, or corn sweeteners, sorbitol, natural and synthetic gums such as gum acacia, tragacanth, sodium alginate, and gum arabic, gelatin, mannitol, starches such as starch paste, corn starch, or potato starch, magnesium trisilicate, talc, keratin, colloidal silica, urea, stearic acid, magnesium stearate, dibasic calcium phosphate, crystalline cellulose, methyl cellulose, carboxymethyl cellulose, polyethylene glycol, waxes, glycerin, and saline solution, among others.

The sustained release formulations of the present invention may also include at least one antiadherent, binder, disintegrant, glidant, lubricant, or other ingredients known for use in pharmaceutical preparations.

Antiadherents may include agents that prevent the sticking of solid dosage formulation ingredients to punches and dies during tableting. Such compounds include, by way of example and without limitation, magnesium stearate, talc, calcium stearate, glyceryl behenate, PEG, hydrogenated vegetable oil, mineral oil, stearic acid, etc.

Binders may include excipients that further contribute to the controlled-release properties of the active agent from the formulation. Binders may include substances used to cause adhesion of powder particles in solid dosage formulations. Such compounds include, by way of example and without limitation, acacia, tragacanth, alginic acid, sodium alginate, carboxymethylcellulose, poly(vinylpyrrolidone), compressible sugars (e.g., NuTab), glucose, corn sweeteners, ethylcellulose, gelatin, albumin, collagen, liquid glucose, methylcellulose, polypropylene glycol, polyoxyethylene-polypropylene copolymer, polyethylene ester, polyethylene sorbitan ester, polyethylene oxide, polyethylene glycol, waxes, poloxamers (e.g. PLURONIC® F68, PLURONIC® F127), povidone, ion exchange resins such as crosslinked acrylate and styrene based ion exchange resins and pregelatinized starch, and other materials known in the art.

Disintegrants include compounds used in solid dosage forms to promote the disruption of the solid mass into smaller particles that are more readily dispersed or dissolved. Exemplary disintegrants may include, without limitation, starches such as corn starch, potato starch, pre-gelatinized and modified starches thereof, sweeteners, clays such as bentonite, microcrystalline cellulose, methyl cellulose, carboxymethylcellulose calcium, sodium carboxymethylcellulose, hydroxy propylcellulose-low substituted, colloidal silicon dioxide, alginic acid, sodium alginate, cellulose polyacrilin potassium, alginates, sodium starch glycolate, gums, agar, guar, locust bean, karaya, xanthan, pectin, tragacanth, agar, bentonite, polyvinylpyrrolidone, combinations thereof, and other materials known in the art.

Glidants are agents used in solid dosage formulations to promote flowability of the solid mass. For example, such compounds may include, without limitation, colloidal silica, cornstarch, talc, calcium silicate, magnesium silicate, colloidal silicon, tribasic calcium phosphate, silicon hydrogel, combinations thereof, and other materials known in the art.

Lubricants include substances used in solid dosage formulations to reduce friction during compression. Such compounds may include, by way of example and without limitation, sodium oleate, sodium stearate, calcium stearate, zinc stearate, magnesium stearate, polyethylene glycol, talc, mineral oil, stearic acid, sodium benzoate, sodium acetate, sodium chloride, combinations thereof, and other materials known in the art.

The sustained release formulation of the present invention may also include at least one acidifying agent, alkalizing agent, antioxidant, buffering agent, or other ingredients known for use in pharmaceutical preparations.

Acidifying agents may include compounds used to provide an acidic medium for product stability. Such compounds include, without limitation, acetic acid, amino acid, citric acid, fumaric acid and other alpha hydroxy acids, hydrochloric acid, ascorbic acid, nitric acid, phosphoric acid, etc.

Alkalizing agents may include compounds used to provide an alkaline medium for product stability. Such compounds include, without limitation, ammonia solutions, ammonium carbonate, diethanolamine, monoethanolamine, potassium hydroxide, sodium borate, sodium carbonate, sodium bicarbonate, sodium hydroxide, triethanolamine, trolamine, etc.

Antioxidants may include agents which inhibit oxidation and thus are used to prevent the deterioration of preparations by oxidative processes. Such compounds include, without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate, sodium metabisulfite, etc.

Buffering agents may include compounds used to buffer changes in pH upon dilution. Such compounds may include, without limitation, potassium metaphosphate, potassium phosphate, monobasic sodium acetate, sodium citrate anhydrous and dehydrate, etc.

Figure 2:
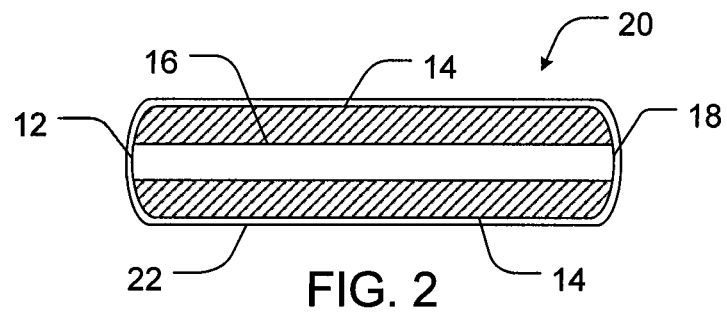
FIG. 2 is a cross-section view of a pharmaceutical tablet in accordance with another embodiment of the present invention.

The sustained release dosage forms according to some aspects of the present invention may further include various coatings. Such coatings may perform any number of functions, including, but not limited to, protecting the oral dosage form from the environment to thus improve stability, masking unpleasant tastes and odors, improving ease of ingestion, improving product identity, facilitating handling during manufacture, improving mechanical integrity to reduce damage, to provide administration of additional active agent, and/or to further regulate the release of the sustained release formulation. As shown in FIG. 2, a pharmaceutical formulation 20 may include a coating 22 to provide any of the above-described characteristics. The coating of the formulation may be accomplished by any means known, including, but without limitation, sugar coating, polymer film coating, microencapsulation, compression coating, etc. Various techniques and coating materials are known in the art. For example, material that may be useful as enteric coatings may include, without limitation, cellulose acetate phthalate, polyvinyl acetate phthalate, hydroxypropylmethyl cellulose phthalate, methacrylic acid-methacrylic acid ester copolymers, cellulose acetate trimellitate, carboxymethylethyl cellulose, hydroxypropylmethyl cellulose acetate succinate, etc., and combinations thereof. Mixtures of waxes, shellac, zein, ethyl cellulose, acrylic resins, cellulose acetate, silicone elastomers, etc., can be used to achieve sustained various release coating. General coating methods can be found in *Remington: The Science and Practice of Pharmacy* 20$^{th}$ ed. (2000), Chapter 46, which is incorporated by reference.

The coating may be primarily protective, and thus provided prolong shelf-life of the pharmaceutical during storage. Additionally, the coating may contain an active agent that is either the same or different from either the first active agent or the at least one second active agent. In one aspect, the active agent contained in the coating 22 may be the same as the first active agent contained in the first layer 12. In this way, the first active agent may begin immediate release from the coating upon ingestion of the oral formulation and provide extended or sustained release from the first layer as the two adjacent layers break down. Additionally, the active agent contained in the coating may exert the same or different therapeutic effect compared to the active agents contained in the first layer and the adjacent layers. For example, a formulation containing sustained release opioid agonists may include additional opioid agonist that is the same or different in the immediate release coating to provide quick $C_{max}$ blood serum levels for pain relief prior to release of the opioid agonist from the first layer.

In another aspect, the coating 22 may be a delayed release coating. As such, initiation of erosion of the adjacent layers may be delayed by the breakdown of the coating 22 following ingestion, thus further controlling the release characteristics of the first and second active agents. Additionally, a controlled release coating may also be applied to only a portion of an outside surface of the adjacent layers. Such a coating may allow the pharmaceutical composition to erode primarily from the edges, and thus provide additional variability to potential release profiles. It should be noted that the delayed release coating may also contain an active agent that may be the same as or different from the first active agent and the at lease one second active agent.

Figure 3:
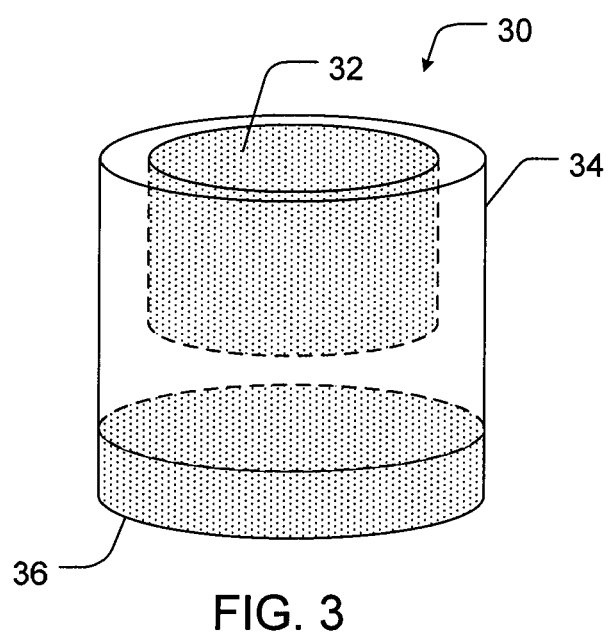
FIG. 3 is a perspective view of a pharmaceutical tablet in accordance with yet another embodiment of the present invention.

Immediate release layers may also be included in the pharmaceutical formulations of the present invention that are distinct from coatings. As shown in FIG. 3, for example, a pharmaceutical tablet 30 may include a first layer 32 containing a first active agent, where the first layer 32 is surrounded by a adjacent layer 34 that blocks access of fluids to a portion of the first layer 32. In this case, the adjacent layer 34 is a single structure that surrounds the first layer 32 on three sides. As has been described, the adjacent layer 34 may contain at least one second active agent for release as the layer erodes. An immediate release layer 36 may be included in the pharmaceutical tablet 30 to provide immediate release of a third active agent. The third active agent may be the same or different from the first active agent or the second active agent. In this particular configuration, the release of the second active agent is not dependent on the immediate release properties of the immediate release layer 36.

EXAMPLES

The following examples of formulations of hydrocodone bitartrate and acetaminophen are provided to promote a more clear understanding of certain embodiments of the present invention, and are in no way meant as a limitation thereon.

Example 1

The following is an example formulation for a 10/500 mg hydrocodone bitartrate/acetaminophen tablet. Each of the portions exemplified below is formulated separately and compressed into a single trilayer tablet having a configuration as shown in FIG. 1. The tablet includes an extended release hydrocodone layer disposed between two extended release acetaminophen layers.

TABLE 1

Hydrocodone Extended Release Layer

| % per dosage unit[1] | % per unit[2] | ingredient | mg/dosage unit |
|---|---|---|---|
| 1.03 | 5.00 | Hydrocodone Bitartrate, USP | 10.00 |
| 1.70 | 8.25 | Ethylcellulose Aqueous Dispersion, NF | 16.50 |
| 8.26 | 40.00 | Ethylcellulose, NF | 80.00 |
| 7.48 | 36.25 | Carnauba Wax, NF | 72.50 |
| 2.06 | 10.00 | Calcium Sulfate Dihydrate, NF | 20.00 |
| 0.10 | 0.50 | Magnesium Stearate, NF | 1.00 |
|  | 100.00 | Average Weight | 200.00 |

[1]Percent (%) of each component present as a total of the average weight of the final dosage form.
[2]Percent (%) of each component present as a total average weight of each intermediate.

TABLE 2

Acetaminophen Extended Release Layers

| | | | mg/dosage unit | | |
|---|---|---|---|---|---|
| % per unit[1] | % per unit[2] | ingredient | Layer I | Layer II | Total (1 + II) |
| 51.60 | 70.32 | Acetaminophen, USP | 295.36 | 204.64 | 500.00 |
| 6.29 | 8.57 | Copolymers of Acrylate and Methacryaltes (EUDRAGIT ®), NF | 35.99 | 24.93 | 60.92 |
| 10.57 | 14.41 | Calcium Sulfate Dihydrate, NF | 60.52 | 41.94 | 102.46 |
| 0.70 | 0.96 | Povidone USP | 4.03 | 2.79 | 6.82 |
| 0.36 | 0.49 | Colloidal Silicon Dioxide, NF | 2.07 | 1.43 | 3.50 |
| 3.30 | 4.50 | Carnauba Wax, NF | 18.90 | 13.10 | 32.00 |
| 0.55 | 0.75 | Magnesium Stearate, NF | 3.13 | 2.17 | 5.30 |
|  | 100.00 | Average Weight | 420.00 | 291.00 | 711.00 |

[1]Percent (%) of each component present as a total of the average weight of the final dosage form.
[2]Percent (%) of each component present as a total average weight of each intermediate.

Example 2

The following is an example formulation for a 15/500 mg hydrocodone bitartrate/acetaminophen extended release tablet having a configuration as shown in FIG. 2. The 10/500 mg hydrocodone bitartrate/acetaminophen extended release tablet of Example 1 was coated with the immediate release hydrocodone bitartrate coating exemplified in Table 3.

TABLE 3

Hydrocodone Immediate Release Coating

| % per dosage unit[1] | % per unit[2] | ingredient | mg/dosage unit |
|---|---|---|---|
| 3.12 | 52.07 | Opadry II Clear | 30.20 |
| 0.50 | 8.62 | Hydrocodone Bitartrate, USP | 5.00 |
| 2.35 | 31.91 | Opadry II White | 22.80 |
|  | 100.00 | Average Weight | 58.00 |
| Total Average Weight of Film Coated Tablet | | | 969.00 |

[1]Percent (%) of each component present as a total of the average weight of the final dosage form.
[2]Percent (%) of each component present as a total average weight of each intermediate.

Example 3

The following is an example of the manufacturing process used to construct the tablets exemplified in Examples 1 and 2.

Figure 4:
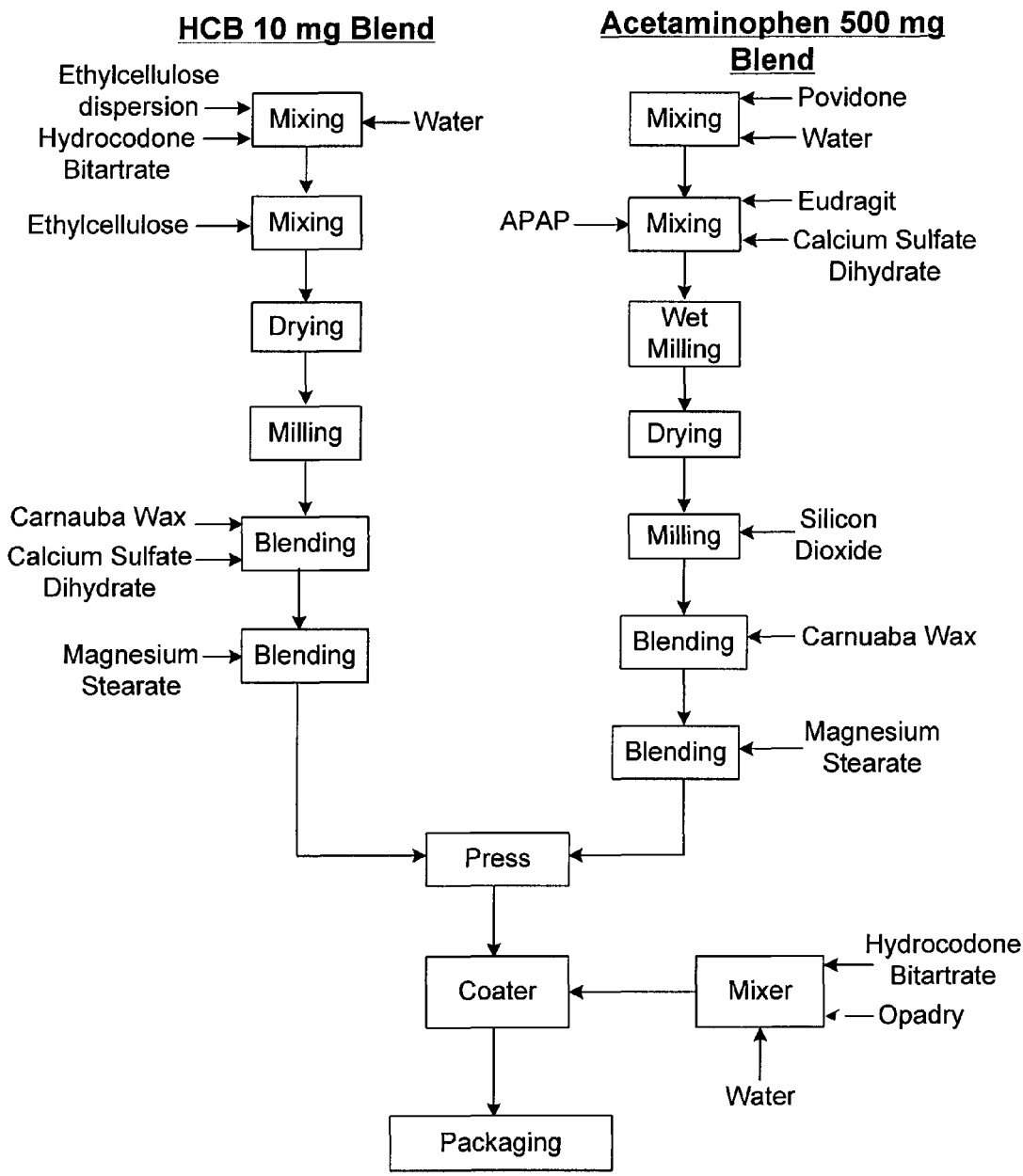
FIG. 4 is a process flow diagram of the manufacture of a tablet presented in accordance a further embodiment of the present invention.

As is shown in FIG. 4, an extended release 10 mg blend of hydrocodone was prepared as follows: hydrocodone bitartrate was granulated in a mixer with an ethyl cellulose aqueous dispersion. Ethyl cellulose was added to the granulation in a mixer. The resulting wet granulation was dried in a dryer, milled, and blended with carnauba wax and calcium sulfate. The resulting blend was lubricated with magnesium stearate.

In a separate blending procedure, an extended release 500 mg blend of APAP was prepared as follows: APAP, calcium sulfate, and copolymers of acrylate and methacrylates (EUDRAGIT®) were mixed in a mixer. The mixture was granulated with an aqueous polyvinylpyrrolidone solution using a mixer. The wet granulation was dried in a dryer, milled with silicon dioxide, and blended with carnauba wax. The resulting blend was lubricated with magnesium stearate.

The resulting blends were compressed into a triple-layered tablet using a press as follows: the bottom layer was filled with approximately 420 mg of the APAP blend, the middle layer was filled with approximately 200 mg of the hydrocodone bitartrate blend, and the top layer was filled with approximately 291 mg of the APAP blend. It has been discovered that the disparity seen between the amount of APAP in each of the top and bottom layers may improve the compressibility of the tablet formulation.

Compressed tablets were then coated with 5 mg of an immediate release hydrocodone bitartrate coating containing commercially available Opadry® polymers.

Example 4

The following is an example of a dissolution profile of the 15/500 mg hydrocodone bitartrate/acetaminophen tablet of Example 2. The example also includes dissolution profiles of the tablet in the presence of alcohol.

Figure 5:
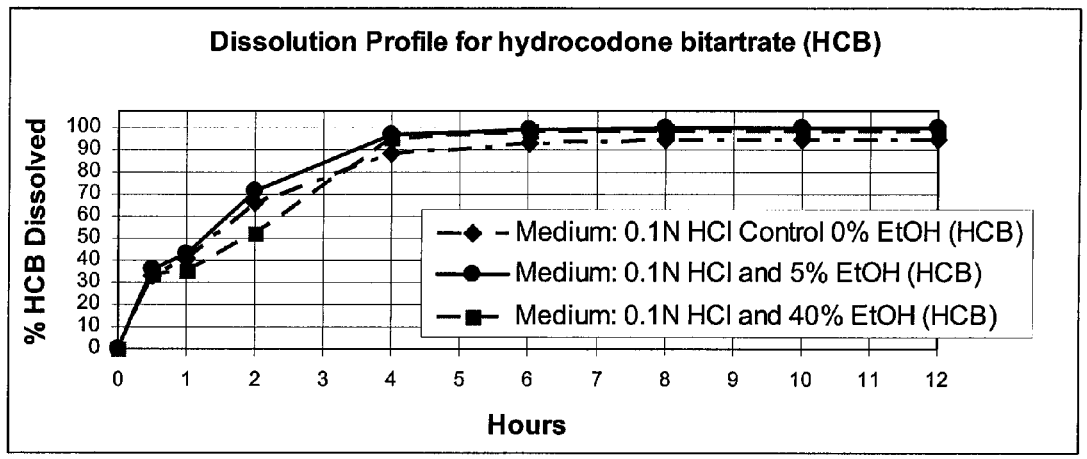
FIG. 5 is a graphical representation of data presented in accordance a yet a further embodiment of the present invention.
Figure 6:
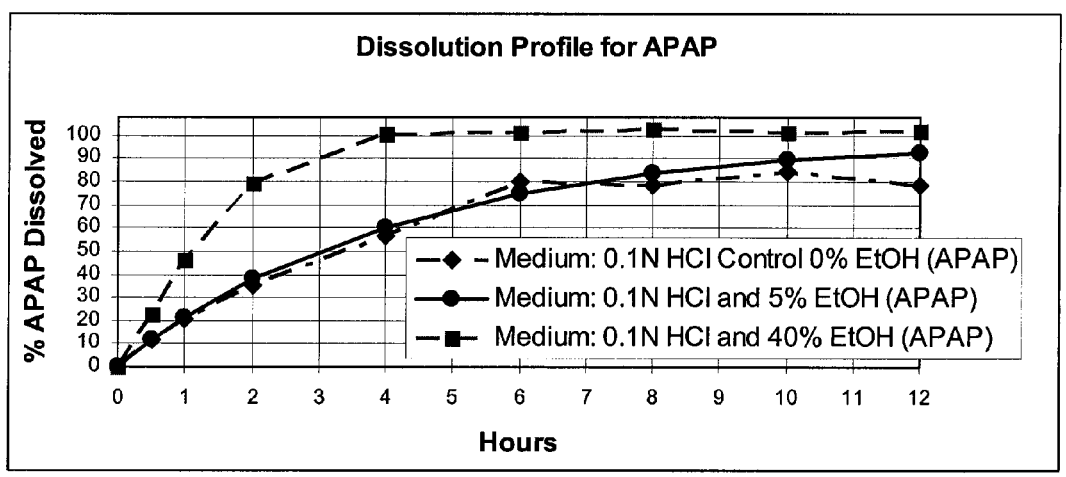
FIG. 6 is a graphical representation of data presented in accordance another embodiment of the present invention.

Dissolution was carried out with the 15/500 mg hydrocodone bitartrate/acetaminophen tablets of Example 2 using USP Apparatus 1 (900 ml) at 100 rpm in three different mediums. Medium 1 was a 0.1N HCl solution with 0% EtOH. Medium 2 was a 0.1N HCl solution with 5% EtOH. Medium 3 was a 0.1N HCl solution with 40% EtOH. As can be seen in FIG. 5, there was very little change in the dissolution profile of the pharmaceutical tablet in the presence of alcohol. Without intending to be bound to a particular theory, the lack of accelerated release of the hydrocodone bitartrate in the presence of alcohol may be due to the acetaminophen layers limiting contact between the hydrocodone bitartrate extended release layer and the dissolution medium. The dissolution profiles of APAP in each of Mediums 1, 2, and 3 are shown in FIG. 6.

Example 5

The 15/500 mg hydrocodone bitartrate/acetaminophen extended release tablet of Example 2 and a control were administered in an open label, single-dose, two-way crossover study in 15 healthy male and female subjects. Each subject received each treatment once with a minimum seven days washout period between treatments. Treatment 1 consisted of an overnight fast of at least 10 hours followed by a standardized high-fat breakfast to be consumed within 30 minutes of dosing. One tablet of the pharmaceutical composition of Example 2, namely a 15/500 Hydrocodone/Acetaminophen extended release tablet, was administered with 240 ml of water 30 minutes after starting the meal. Treatment 2 consisted of an overnight fast of at least 10 hours followed by administration of one tablet of Example 2 with 240 ml of water. Treatment 3 consisted of an overnight fast of at least 10 hours followed by administration of one 10/500 LORTAB® tablet.

TABLE 4

Summary of Pharmacokinetics Data of Example 2.

| PK Parameter | 15/500 Hydrocodone/Acetaminophen ER | | | | 10/500 LORTAB ® | |
|---|---|---|---|---|---|---|
| | Treatment 1 (Fed; n = 15) | | Treatment 2 (Fasted; n = 15) | | Treatment 3 (Fasted; N = 15) | |
| | HC | APAP | HC | APAP | HC | APAP |
| $C_{max}$ (ng/ml) | 23.4 | 3606.0 | 20.3 | 2544.0 | 22.4 | 7241.0 |
| $AUC_{0-8}$ (ng · hr/ml) | 122.0 | 15100.0 | 111.0 | 13046.0 | 109.0 | 23591.0 |
| $AUC_{0-12}$ (ng · hr/ml) | 169.0 | 19761.0 | 154.0 | 16868.0 | 130.0 | 25686.0 |
| $AUC_{0-24}$ (ng · hr/ml) | 220.0 | 23421.0 | 207.0 | 20847.0 | 150.0 | 27550.0 |
| $AUC_{inf}$ (ng · hr/ml) | 235.0 | 246666.0 | 223.0 | 26587.0 | 156.0 | 28474.0 |
| $T_{max}$ (median hrs) | 5.0 | 4.5 | 4.5 | 3.5 | 1.3 | .05 |

Figure 7:
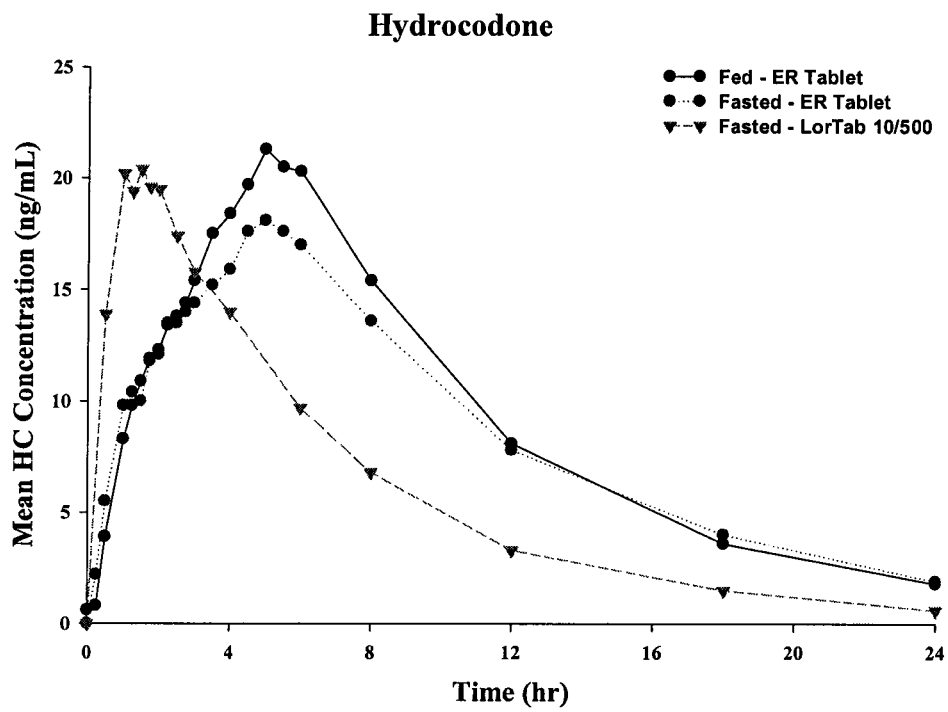
FIG. 7 is a graphical representation of data presented in accordance a yet another embodiment of the present invention.
Figure 8:
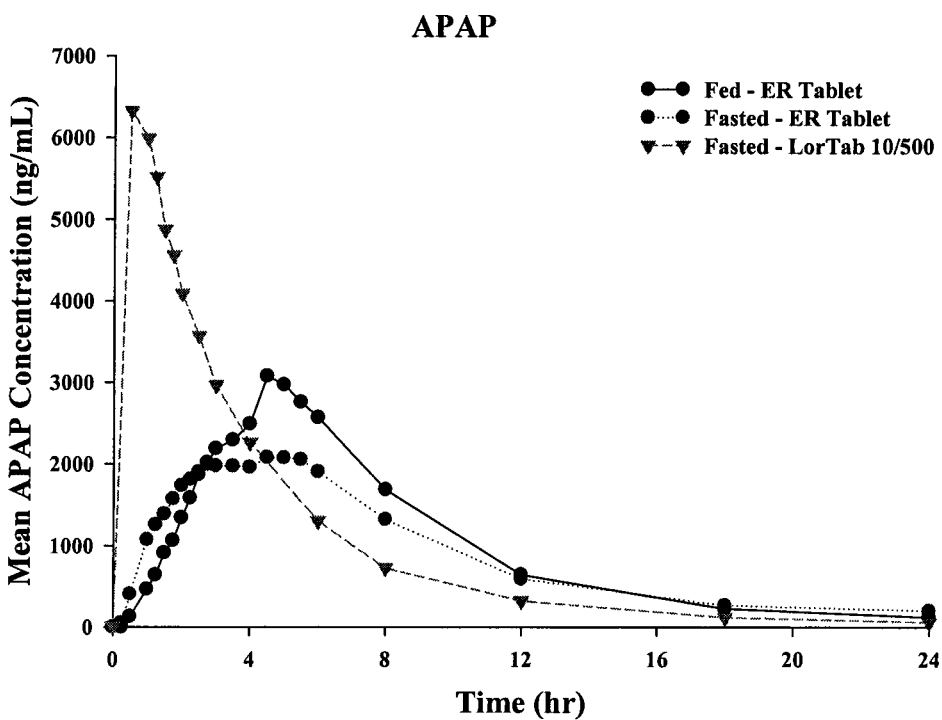
FIG. 8 is a graphical representation of data presented in accordance a further embodiment of the present invention.

Table 4 and FIGS. 7 and 8 show the results of the study. Note that $T_{max}$ for both hydrocodone and acetaminophen is significantly greater for the formulation of Example 2 than for the LORTAB® formulation.

Example 6

Table 5 shows a formulation of hydrocodone bitartrate/APAP that was manufactured to have a configuration as shown in FIG. 3.

TABLE 5

7.5/243.75 mg hydrocodone/acetaminophen tablet, Test Product A.

| Ingredient | mg/dosage unit |
|---|---|
| Hydrocodone Bitartrate Immediate Release Portion | |
| Hydrocodone Bitartrate, USP | 2.50 |
| Lactose Hydrous, NF | 52.00 |
| Microcrystalline Cellulose | 22.14 |
| Sodium Starch Glycolate, NF | 1.60 |

TABLE 5-continued 7.5/243.75 mg hydrocodone/acetaminophen tablet, Test Product A.

| Ingredient | mg/dosage unit |
|---|---|
| Povidone USP | 1.20 |
| Microcrystalline Cellulose | 20.00 |
| Magnesium Stearate, NF | 0.56 |
| Hydrocodone Bitartrate Extended Release Portion | |
| Hydrocodone Bitartrate, USP | 5.00 |
| Ethylcellulose Aqueous Dispersion, NF | 8.25 |
| Ethylcellulose, NF | 40.00 |
| Carnauba Wax, NF | 46.25 |
| Magnesium Stearate, NF | 0.50 |
| Acetaminophen Extended Release Portion | |
| Acetaminophen, USP | 243.75 |
| Copolymers of Acrylate and Methacryaltes (EUDRAGIT ®), NF | 29.70 |
| Calcium Sulfate Dihydrate, NF | 49.95 |
| Povidone USP | 3.30 |
| Colloidal Silicon Dioxide, NF | 1.65 |
| Magnesium Stearate, NF | 1.65 |
| Total Average Weight/Unit | 530.00 |

Table 6 shows a formulation of hydrocodone bitartrate/APAP that was manufactured to have a configuration as shown in FIG. 1.

TABLE 6

7.5/243.75 mg hydrocodone/acetaminophen tablet, Test Product B.

| Hydrocodone Bitartrate Extended Release Portion | |
|---|---|
| Hydrocodone Bitartrate, USP | 7.50 |
| Ethylcellulose Aqueous Dispersion, NF | 12.38 |
| Ethylcellulose, NF | 60.00 |
| Carnauba Wax, NF | 69.37 |
| Magnesium Stearate, NF | 0.75 |
| Acetaminophen Extended Release Portion | |
| Acetaminophen, USP | 243.75 |
| Copolymers of Acrylate and Methacryaltes (EUDRAGIT ®), NF | 29.70 |
| Calcium Sulfate Dihydrate, NF | 49.95 |
| Povidone USP | 3.30 |
| Colloidal Silicon Dioxide, NF | 1.65 |
| Magnesium Stearate, NF | 1.65 |
| Total Average Weight/Unit | 480.00 |

Example 7

A randomized, single-dose, four-way crossover study was performed on 17 healthy male subjects under fasting conditions. Following an overnight fast on study days 1, 8, 15, and 22, subjects were sequentially dosed at 1 minute intervals with either 1) a single oral dose of two tablets of Test Product A from Table 5; 2) a single oral dose of two tablets of Test Product B from Table 6; 3) an oral dose of one tablet of Reference Product C from Table 7 every four hours for a total of 3 doses; or 4) a single oral dose of one tablet of Reference Product D from Table 7.

TABLE 7

Reference Product

| Reference Product C | VICODIN ® tablets; hydrocodone bitartrate 5 mg with acetaminophen 500 mg; Knoll Laboratories |
|---|---|

TABLE 7-continued

Reference Product

| | |
|---|---|
| Reference Product D | TYLENOL ARTHRITIS PAIN ® Extended Relief Caplets; acetaminophen extended release 650 mg; McNeil Consumer Healthcare |

Serial blood samples were collected for up to 24 hours from each subject after each treatment. Samples were analyzed for hydrocodone and acetaminophen concentrations using high performance liquid chromatographic mass spectrometric methods. Table 8 provides geometric means for the hydrocodone pharmacokinetic data for the study.

TABLE 8

Hydrocodone Pharmacokinetic Data

| Treatment | $C_{max}$ (ng/mL) | $AUC_{0-8}$[1] | $AUC_{0-12}$[1] | $AUC_{0-24}$[1] | $AUC_{inf}$[1] |
|---|---|---|---|---|---|
| Test Product A | 19.38 | 109.69 | 150.41 | 202.46 | 222.82 |
| % Ratio: Product A/ Reference C | 106.19 | 128.26 | 105.89 | 97.4 | 100.97 |
| Test Product B | 16.48 | 88.92 | 128.29 | 184.21 | 215.22 |
| % Ratio: Product B/ Reference C | 90.3 | 103.98 | 90.31 | 88.62 | 97.52 |
| Reference Product C | 18.25 | 85.52 | 142.05 | 207.87 | 220.69 |

[1]AUC measurements in ng-hr/mL

Figure 9:
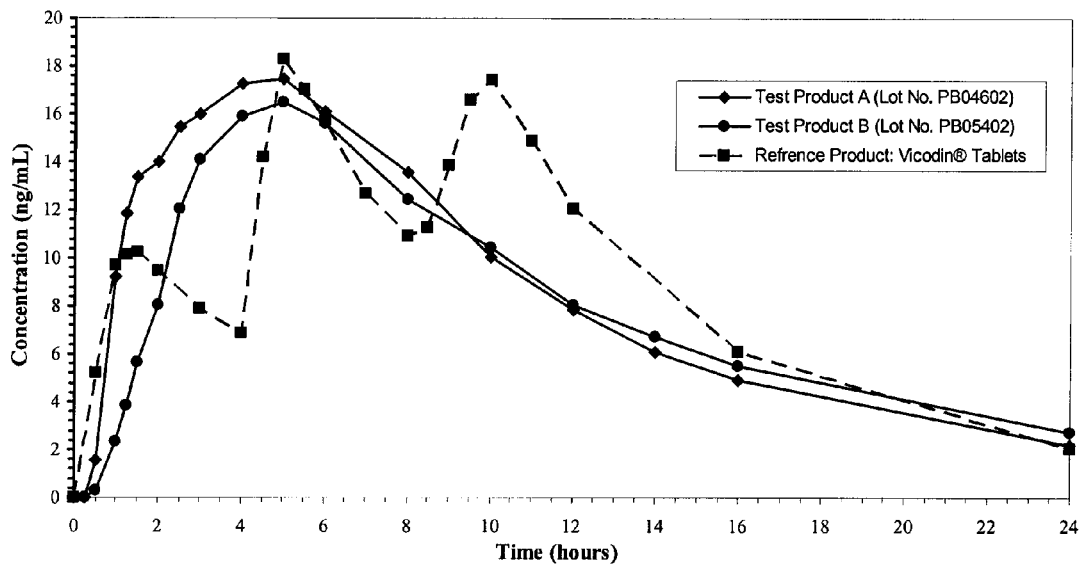
FIG. 9 is a graphical representation of data presented in accordance a further embodiment of the present invention.

FIG. 9 shows a plot of the mean plasma hydrocodone concentration for Test Product A, Test Product B, and Reference Product C. Note that Test Product A and Test Product B show single peaks representing the single administration dose with a considerably longer time course than a single dose of Reference Product C, represented by a single peak on the graph. Note that $T_{max}$ is at least greater than 3 hours for Test Product A and at least greater than 4 hours for Test Product B.

Table 9 provides acetaminophen pharmacokinetic data for the study.

TABLE 9

Acetaminophen Pharmacokinetic Data

| Treatment | $C_{max}$ (ng/mL) | $AUC_{0-8}$[1] | $AUC_{0-12}$[1] | $AUC_{0-24}$[1] | $AUC_{inf}$[1] |
|---|---|---|---|---|---|
| Test Product A | 2375.02 | 12333.97 | 15.902.79 | 20867.03 | 24474.33 |
| % Ratio: Product A/ Reference D | 36.56 | 45.31 | 51.00 | 59.80 | 68.35 |
| Test Product B | 4155.93 | 16809.10 | 20130.45 | 23874.42 | 25307.08 |
| % Ratio: Product B/ Reference D | 63.97 | 61.75 | 64.56 | 68.42 | 70.67 |
| Reference Product D | 6496.31 | 27221.46 | 31180.84 | 34892.43 | 35807.95 |

[1]AUC measurements in ng-hr/mL

Figure 10:
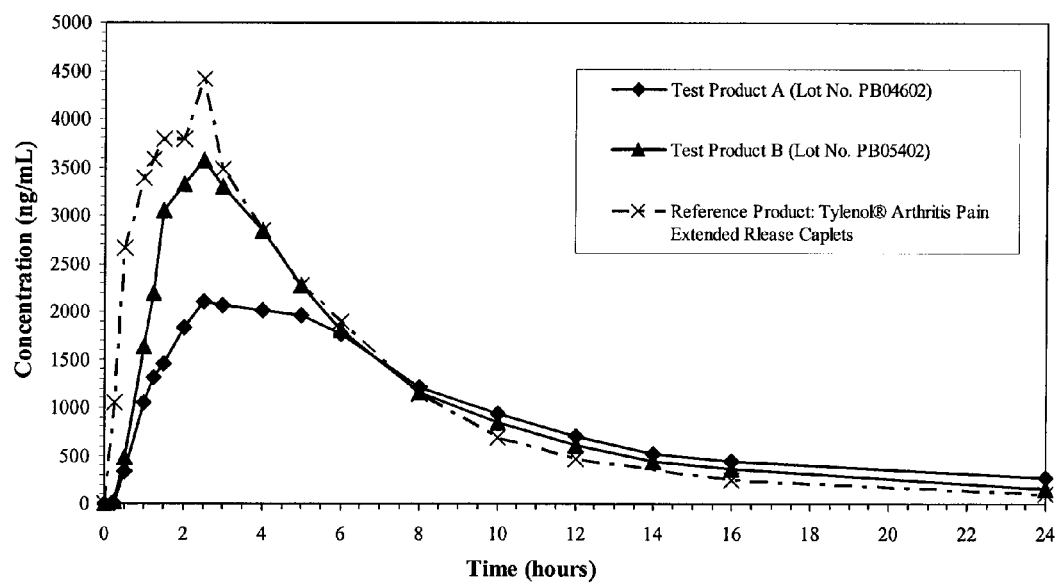
FIG. 10 is a graphical representation of data presented in accordance yet a further embodiment of the present invention.

FIG. 10 shows a plot of the mean plasma acetaminophen concentration for Test Product A, Test Product B, and Reference Product D.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A sustained release oral dosage pharmaceutical tablet, comprising:
   a. a first layer consisting of:
      i. a first active agent comprising hydrocodone or a pharmaceutically acceptable salt thereof to be released over a sustained period of time;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof; and
      iii. carnauba wax;
   b. at least two adjacent controlled release layers wherein at least one of said two adjacent controlled release layers consists of:
      i. at least one second active agent comprising acetaminophen;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof;
      iii. copolymers of acrylate and methacrylates; and
      iv. carnauba wax;
   said at least two adjacent layers being configured to regulate fluid access to a portion of the first layer, thereby controlling release of the first active agent from the first layer over the sustained period of time,
   wherein the configuration of the first layer and the two adjacent controlled release layers provides a $T_{max}$ hydrocodone serum concentration occurring at from about 3 hours to about 8 hours after administration of the tablet to the subject and a $T_{max}$ acetaminophen serum concentration occurring at from about 2 hours to about 8 hours after administration of the tablet to the subject; and
   wherein fluid access is regulated in an amount sufficient to release the first active agent at a rate of from about 30% to about 45% after about 1 hour, from about 43% to about 75% after about 2 hours, and from about 80% to about 100% after about 4 hours.

2. The tablet of claim 1, wherein a portion of the two adjacent layers are joined into a single continuous layer.

3. The tablet of claim 1, wherein the two adjacent layers cover substantially the entire first layer around a peripheral edge thereof.

4. The tablet of 1 wherein the hydrocodone is selected from the group consisting of hydrocodone bitartrate, hydrocodone bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone hemipentahydrate, hydrocodone pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis(heptafluorobutyrate), hydrocodone bis(m-ethylcarbamate), hydrocodone bis(pentafluoropropionate), hydrocodone bis(pyridine carboxylate), hydrocodone bis(trifluoroacetate), hydrocodone chlorhydrate, hydrocodone sulfate pentahydrate and combinations thereof.

5. The tablet of claim 1, further comprising an immediate release layer having a third active agent.

6. The tablet of claim 5, wherein the third active agent and either of the first active agent and the second active agent are the same.

7. The tablet of claim 5, wherein the third active agent is hydrocodone.

8. The tablet of claim 5, wherein the immediate release layer is an immediate release coating substantially surrounding the pharmaceutical tablet.

9. The tablet of claim 1, wherein the two adjacent layers are erodible layers.

10. The tablet of claim 1, wherein each of the two adjacent layers contains acetaminophen.

11. The tablet of claim 1, wherein the at least two adjacent layers are configured to expose only a peripheral edge of the first layer from which the first active agent is released.

12. The tablet of claim 1, wherein the at least two adjacent layers are configured such that the peripheral edge of the first layer provides constant release of the first active agent.

13. The tablet of claim 1, wherein the configuration of the first layer and the at least two adjacent layers provides a $T_{max}$ hydrocodone serum concentration at from about 4 hours to about 8 hours after administration of the tablet to the subject.

14. The tablet of claim 1, wherein the configuration of the first layer and the at least two adjacent layers provides a $T_{max}$ hydrocodone serum concentration at from about 4 hours to about 6 hours after administration of the tablet to the subject.

15. The tablet of claim 1, wherein fluid access is regulated in an amount sufficient to release the first active agent at a rate of from about 37% to about 44% after about 1 hour, from about 60% to about 73% after about 2 hours, and from about 85% to about 97% after about 4 hours.

16. The tablet of claim 1, wherein fluid access is regulated in an amount sufficient to release the first active agent at a rate of from about 39% to about 42% after about 1 hour, from about 65% to about 70% after about 2 hours, and from about 87% to about 94% after about 4 hours.

17. The tablet of claim 1, that exhibits a mean plasma hydrocodone concentration profile under fed and fasting conditions similar to the profile shown in FIG. 7 and a mean plasma acetaminophen concentration profile under fed and fasting conditions similar to the profile shown in FIG. 8.

18. The tablet of claim 1, that exhibits a mean plasma hydrocodone concentration profile similar to the profile shown in FIG. 9 for Test Product A or Test Product B.

19. The tablet of claim 1, that exhibits a mean plasma acetaminophen concentration profile similar to the profile shown in FIG. 10 for Test Product A or Test Product B.

20. A pharmaceutical tablet that limits alcohol-induced accelerated release of an active agent, comprising:
   a. a first layer consisting of:
      i. a first active agent comprising hydrocodone or a pharmaceutically acceptable salt thereof;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof; and
      iii. carnauba wax;
   b. at least two adjacent layers wherein at least one of said two adjacent layers consists of:
      i. at least one second active ingredient comprising acetaminophen;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof;
      iii. copolymers of acrylate and methacrylates; and
      iv. carnauba wax;
   wherein the first layer is disposed between the two adjacent layers, the two adjacent layers covering a portion of the first layer such that the tablet provides a release rate of the first active agent into an in vitro solution of from about 30% to about 50% after about 1 hour, from about 45% to about 75% after about 2 hours, and from about 80% to about 100% after about 4 hours, said in vitro solution including from about 5% ethanol to about 40% ethanol; and wherein a $T_{max}$ acetaminophen serum concentration occurs at from about 2 hours to about 8 hours after administration of the tablet to the subject.

21. The tablet of claim 20, wherein the two adjacent layers cover a portion of the first layer such that the tablet provides a release rate of the first active agent into an in vitro solution of from about 37% to about 48% after about 1 hour, from about 65% to about 75% after about 2 hours, and from about 90% to about 100% after about 4 hours, said in vitro solution including from about 5% ethanol to about 40% ethanol.

22. The tablet of claim 20, wherein the two adjacent layers cover a portion of the first layer such that the tablet provides a release rate of the first active agent into an in vitro solution of from about 40% to about 46% after about 1 hour, from about 68% to about 73% after about 2 hours, and from about 90% to about 98% after about 4 hours, said in vitro solution including from about 5% ethanol to about 40% ethanol.

23. The tablet of claim 20 that exhibits a mean plasma hydrocodone concentration profile under fed and fasting conditions similar to the ER Tablet profile shown in FIG. 7 and a mean plasma acetaminophen concentration profile under fed and fasting conditions similar to the ER Tablet profiles shown in FIG. 8.

24. The tablet of claim 20 that exhibits a mean plasma hydrocodone concentration profile as shown in FIG. 9 for Test Product A or Test Product B.

25. The tablet of claim 20 that exhibits a mean plasma acetaminophen concentration profile as shown in FIG. 10 for Test Product A or Test Product B.

26. A sustained release oral dosage pharmaceutical tablet, comprising:
   a. a first layer consisting of:
      i. a first active agent comprising hydrocodone or a pharmaceutically acceptable salt thereof to be released over a sustained period of time;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof; and
      iii. carnauba wax;
   b. at least two adjacent controlled release layers consisting of:
      i. acetaminophen;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof;
      iii. copolymers of acrylate and methacrylates; and
      iv. carnauba wax;
   said at least two adjacent layers being configured to regulate fluid access to a portion of the first layer, thereby controlling release of the first active agent from the first layer over the sustained period of time, and
   c. optionally, an immediate release layer of hydrocodone or pharmaceutically acceptable salt;
   wherein the configuration of the first layer and the two adjacent controlled release layers provides a $T_{max}$ hydrocodone serum concentration occurring at from about 3 hours to about 8 hours after administration of the tablet to the subject and a $T_{max}$ acetaminophen serum concentration occurring at from about 2 hours to about 8 hours after administration of the tablet to the subject; and
   wherein fluid access is regulated in an amount sufficient to release the first active agent at a rate of from about 30% to about 45% after about 1 hour, from about 43% to about 75% after about 2 hours, and from about 80% to about 100% after about 4 hours.

27. A pharmaceutical tablet that limits alcohol-induced accelerated release of an active agent, consisting of:
   a. a first layer consisting of:
      i. a first active agent comprising hydrocodone or a pharmaceutically acceptable salt thereof;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof; and
      iii. carnauba wax;
   b. at least two adjacent layers consisting of:
      i. acetaminophen;
      ii. a carrier selected from the group consisting of lactose, starch, sucrose, glucose, dextrose, kaolin, microcrystalline cellulose, ethyl cellulose, methyl cellulose, stearic acid, magnesium stearate, dicalcium phosphate, gums, calcium sulfate, calcium carbonate, magnesium carbonate, sodium carbonate, sodium chloride, calcium phosphate, mannitol, sorbitol, inositol, talc, polyethylene glycol, polyvinylpyrrolidone, carboxyalkyl cellulose and combinations thereof;
      iii. copolymers of acrylate and methacrylates; and
      iv. carnauba wax; and
   c. optionally, an immediate release layer of hydrocodone or pharmaceutically acceptable salt;
   wherein the first layer is disposed between the two adjacent layers, the two adjacent layers covering a portion of the first layer such that the tablet provides a release rate of the first active agent into an in vitro solution of from about 30% to about 50% after about 1 hour, from about 45% to about 75% after about 2 hours, and from about 80% to about 100% after about 4 hours, said in vitro solution including from about 5% ethanol to about 40% ethanol; and wherein a $T_{max}$ acetaminophen serum concentration occurs at from about 2 hours to about 8 hours after administration of the tablet to the subject.

* * * * *